United States Patent [19]

Middleton

[11] 4,311,651
[45] Jan. 19, 1982

[54] FLUOROALKOXYSULFUR FLUORIDES

[75] Inventor: William J. Middleton, Chadds Ford, Pa.

[73] Assignee: E. I. Du Pont de Nemours and Company, Wilmington, Del.

[21] Appl. No.: 148,209

[22] Filed: May 9, 1980

[51] Int. Cl.³ .................. C07C 143/00; C07C 147/00
[52] U.S. Cl. .............................. 260/543 H; 568/27; 568/842; 568/939; 568/940; 260/239 BD
[58] Field of Search ...................... 260/543 H; 568/27

[56] References Cited

U.S. PATENT DOCUMENTS 3,418,337 12/1968 Middleton .................. 260/347.8
3,888,924 6/1975 Middleton .................. 260/543 F
3,914,265 10/1975 Middleton .................. 260/397.3

OTHER PUBLICATIONS

Baum, K, J.A.C.S. 91 4594 (1969).
Darragh, J. I. et al., J.C.S. Dalton Trans., 1975, 218.
Darragh J. I. et al., Angew. Chem. Int. 9, 73 (1970).
Middleton, W. J., J. Org. Chem. 40, No. 5 pp. 574–578 (1975).

Primary Examiner—Paul J. Killos
Attorney, Agent, or Firm—James A. Costello

[57] ABSTRACT

Fluoroalkoxysulfur fluorides of the formula

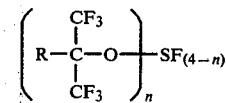

wherein R is H, $CH_3$, $CF_3$, or $C_2F_5$, and n is 1 or 2; their preparation by reaction of lithium fluoroalkoxides with sulfur tetrafluoride; their use as fluorinating agents to replace OH groups in organic molecules with F; and halocarbon solutions of lithium fluoroalkoxides.

13 Claims, No Drawings

FLUOROALKOXYSULFUR FLUORIDES

BACKGROUND OF THE INVENTION

1. Field of the Invention

This invention relates to fluoroalkoxysulfur fluorides, their preparation and use as fluorinating agents to replace hydroxyl groups with fluorine in organic molecules. Also of concern are solutions of the intermediate lithium fluoroalkoxides in halocarbon solvents.

2. State of the Art

Baum, in J. Am. Chem. Soc., 91, 4594 (1969), describes the preparation of 2-fluoro-2,2-dinitroethoxysulfur trifluoride by reaction of 2-fluoro-2,2-dinitroethanol with sulfur tetrafluoride. This compound would not have utility as a fluorinating agent because its two nitro groups would make it explosive. Furthermore, isolation of fluorinated reaction products from a reaction mixture containing this compound would be complicated by its low volatility and that of its expected by-products.

Darragh et al, in J. Chem. Soc., Dalton Trans., 1975, 218, describe the preparation of several aryloxysulfur trifluorides and diaryloxysulfur difluorides by the reaction of aryl silyl ethers and sulfur tetrafluoride. These compounds would not have fluorinating utility because they are generally unstable. In addition, the isolation of fluorinated reaction products, if formed, from reaction mixtures containing the aryloxysulfur trifluorides, would be complicated by the low volatility of the aryloxysulfur trifluorides and their expected by-products. The authors state that they made unsuccessful attempts to prepare alkoxy derivatives of sulfur (IV) fluorides.

Among the most useful known fluorinating agents are the dialkylaminosulfur trifluorides (DAST) of U.S. Pat. No. 3,914,265 and the bis(dialkylamino)sulfur difluorides of U.S. Pat. No. 3,888,924. The fluoroalkoxysulfur fluorides of this invention offer certain advantages over these known fluorinating agents because they are safer to use at elevated temperatures, they are more soluble in non-polar solvents, and aqueous work-up can be avoided because the by-products are volatile.

SUMMARY OF THE INVENTION

The compounds of this invention are fluoroalkoxysulfur fluorides of the formula:

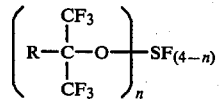

wherein R is selected from H, CH$_3$, CF$_3$ and C$_2$F$_5$, and n is 1 or 2.

The compounds of this invention are prepared by reacting lithium salts of fluoroalcohols with sulfur tetrafluoride according to the sequnce:

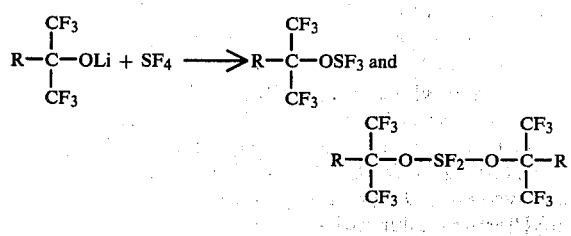

wherein R is as defined above.

The fluoroalkoxysulfur fluorides of this invention are useful as fluorinating agents. In particular, they are useful for replacing hydroxyl groups of organic compounds with fluorine atoms, and can be used in the preparation of fluorine-containing pharmaceuticals. Typical fluorination reactions involve contacting the fluoroalkoxysulfur fluoride of this invention with a solution of the organic hydroxyl compound in a volatile, inert solvent and then isolating the product in nearly pure form by evaporating the solvent.

Another aspect of this invention concerns novel solutions of the intermediate lithium fluoroalkoxides in halocarbon solvent. Such solutions have not been reported previously and the fact that they can be made is interesting in view of the fact that alkali metal alkoxides are generally insoluble in nonpolar solvents.

DETAILS OF THE INVENTION

Preparation of compounds of this invention is conducted by adding a solution of the lithium salt in an inert solvent to a solution of sulfur tetrafluoride in the same or different inert solvent. Suitable inert solvents are those which are liquid at the reaction temperature and include halogenated hydrocarbons, such as CFCl$_3$, CH$_2$Cl$_2$ and CHCl$_3$, and ethers such as dibutyl ether, diethyl ether, and 1,3-dimethoxybenzene. Reaction temperatures can vary between about $-20°$ and $-100°$ C.; the preferred range for best yield is about $-40°$ to $-80°$ C. Pressure is not critical, but atmospheric pressure is preferred for convenience.

The molar ratio of lithium salt to sulfur tetrafluoride will usually vary from about 3:1 to 1:10, respectively. Such ratios, however, are not a necessity. In general, an excess of the lithium salt favors the production of the bis(alkoxy)sulfur difluoride, (n=2), and an excess of sulfur tetrafluoride favors the production of the mono-(alkoxy)sulfur trifluoride, (n=1), although in many cases, both products are formed at the same time. The products are isolated from the reaction mixture by distillation, either at atmospheric pressure or reduced pressure.

Representative hydroxyl compounds which can be fluorinated by the process of this invention include monofunctional and polyfunctional aliphatic primary, secondary, and tertiary alcohols, all of which can contain other substituents. Examples are benzyl alcohol, phenylethyl alcohol, stearyl alcohol, cholesterol, polyvinyl alcohol, and more complex hydroxyl compounds such as cephalosporins (e.g., benzhydryl 3-hydroxymethyl-7-(2-thienylacetamido)-3-cephem-4-carboxylate-1-oxide) and benzodiazepines (e.g., temazepam).

The following Examples illustrate the invention and the preparations illustrate the making of lithium salt intermediates. Temperatures are in degrees Centigrade.

PREPARATION A

Lithium 1,1,1,3,3,3-Hexafluoroisopropoxide $$(CF_3)_2CHOH + BuLi \rightarrow (CF_3)_2CHOLi + BuH$$

A stirred mixture of 168 g (1 mol) of 1,1,1,3,3,3-hexafluoroisopropanol and 300 ml of hexane was cooled to 10°, and one mole of butyllithium in hexane (1.6 M) was added dropwise, keeping the temperature between 10° and 20°. The solid that formed was collected on a filter (under nitrogen) and washed with hexane to give 128.2 g of white powder. A second crop of 23.63 g was obtained by concentrating the hexane filtrate. In total, 151.83 g (87%) of lithium 1,1,1,3,3,3-hexafluoroisopropoxide was obtained as a white, hygroscopic powder, mp 144° (d); $^1$H NMR (CFCl$_3$) δ 4.34 ppm (septet, J=5 Hz); $^{19}$F NMR (CDCl$_3$) δ −79.0 ppm (d, J=5 Hz).

Anal. Calcd. for C$_3$HF$_6$LiO: F, 65.52. Found: F, 65.61.

PREPARATION B

Lithium 2,2,2-Trifluoro-1,1-bis(trifluoromethyl)ethoxide $$(CF_3)_3COH + BuLi \rightarrow (CF_3)_3COLi + BuH$$

A stirred mixture of 11.8 g (0.05 mol) of 2,2,2-trifluoro-1,1-bis(trifluoromethyl)ethanol in 40 ml of hexane was cooled to −10°, and 0.05 mol of butyllithium in hexane (1.6 M) was added dropwise. The reaction mixture was warmed to 25°, and the solid precipitate was collected on a filter and dried under a stream of dry nitrogen to give 10.69 g (88%) of lithium 2,2,2-trifluoro-1,1-bis(trifluoromethyl)ethoxide, mp 139° to 141° (dec.).

Anal. Calcd. for C$_4$F$_9$OLi: F, 70.66. Found: F, 70.27.

EXAMPLE 1

2,2,2-Trifluoro-1-(trifluoromethyl)ethoxysulfur Trifluoride ti $(CF_3)_2CHOLi + SF_4 \rightarrow (CF_3)_2CHOSF_3 + LiF$ A solution of 66.1 g (0.38 mol) of lithium 1,1,1,3,3,3-hexafluoroisopropoxide in 200 ml of dibutyl ether was added dropwise to a solution of 30 ml (measured at −78°, 0.54 mol) of SF$_4$ in 100 ml of dibutyl ether cooled to −70°. The reaction mixture was warmed to room temperature, and the volatile material was distilled out at reduced pressure into a trap cooled to −78°. The distillate was redistilled at atmospheric pressure in a spinning band still to give 26.36 g (27%) of 2,2,2-trifluoro-1-(trifluoromethyl)ethoxysulfur trifluoride as a colorless, fuming liquid: bp 57° to 59°; $^{19}$F NMR (CFCl$_3$) δ −74.1 ppm (d, J=5 Hz,6F), +29.9 ppm (t, J=73 Hz,1F) and +77.9 ppm (d, J=73 Hz,2F).

Anal. Calcd. for C$_3$HF$_9$OS: F, 66.77; S, 12.52. Found: F, 66.57; S, 12.12.

EXAMPLE 2

Bis[2,2,2-trifluoro-1-(trifluoromethyl)ethoxy]sulfur Difluoride

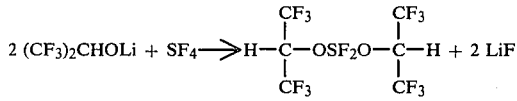

A solution of 66.1 g (0.38 mol) of lithium 1,1,1,3,3,3-hexafluoroisopropoxide in 100 ml of CFCl$_3$ was added dropwise to a solution of 30 ml (measured at −78°, 0.54 mol) of sulfur tetrafluoride in 100 ml of CFCl$_3$ cooled to −70°. The reaction mixture was warmed to room temperature, filtered to remove the precipitated solid, and then distilled to give 18.14 g (24%) of bis[2,2,2-trifluoro-1-(trifluoromethyl)ethoxy]sulfur difluoride as a colorless liquid, bp 37° to 39° (23 mm); $^1$H NMR (CFCl$_3$ 5.58 ppm (m); $^{19}$F NMR (CFCl$_3$) δ −73.9 ppm (d, J=5 Hz, 12F) and +63.1 ppm (2F).

Anal. Calcd. for C$_6$H$_2$F$_{12}$O$_2$S: F, 65.82; S, 7.94. Found: F, 66.03; S, 8.33.

EXAMPLE 3

2,2,2-Trifluoro-1-(trifluoromethyl)ethoxysulfur Trifluoride

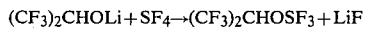

A solution of 33.0 g (0.16 mol) of lithium 1,1,1,3,3,3-hexafluoroisopropoxide in 100 ml of 1,3-dimethoxybenzene was added dropwise to a solution of 30 ml (measured at −78°, 0.54 mol) of sulfur tetrafluoride in 100 ml of 1,3-dimethoxybenzene cooled to −50°. The reaction mixture was warmed to 25°, and the volatile material was distilled out at reduced pressure into a trap cooled to −78°. The distillate was redistilled through a spinning band still, with care being taken to keep the pot temperature below 70°, to give 26.4 g (54%) of 2,2,2-trifluoro-1-(trifluoromethyl)ethoxysulfur as a colorless, fuming liquid, bp 57° to 59°; and 4.5 g of bis[2,2,2-trifluoro-1-(trifluoromethyl)ethoxy]sulfur difluoride as a colorless, fuming liquid, bp 45° to 50° (50 mm).

EXAMPLE 4

Bis[2,2,2-trifluoro-1-(trifluoromethyl)ethoxysulfur Difluoride

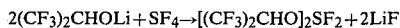

A solution of 33.0 g (0.16 mol) of lithium 1,1,1,3,3,3-hexafluoroisopropoxide in 100 ml of 1,3-dimethoxybenzene was added dropwise to a solution of 4.5 ml (measured at −78°, 0.08 mol) of sulfur tetrafluoride in 50 ml of 1,3-dimethoxybenzene cooled to −50°. The reaction material was warmed to 25°, and the volatile material was distilled out at reduced pressure into a trap cooled to −78°. The distillate was redistilled to give 8.78 g (30%) of bis[2,2,2-trifluoro-1-(trifluoromethyl)ethoxy]sulfur difluoride as a colorless liquid, bp 42° to 44° (40 mm).

EXAMPLE 5

2,2,2-Trifluoro-1,1-bis(trifluoromethyl)ethoxysulfur Trifluoride and
Bis[2,2,2-trifluoro-1,1-bis(trifluoromethyl)ethoxy]sulfur Difluoride

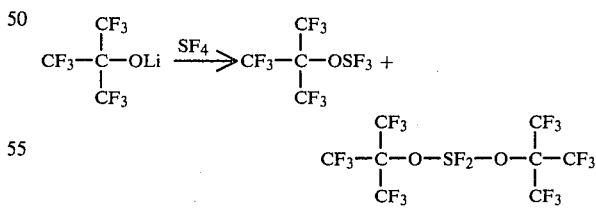

A solution of 10.5 g (0.043 mol) of lithium 2,2,2-trifluoro-1,1-bis(trifluoromethyl)ethoxide in 60 ml of dibutyl ether was added dropwise to a solution of 8 ml (measured at −78° C., 0.15 mol) of sulfur tetrafluoride in 50 ml of dibutyl ether cooled to −70° C. The reaction mixture was warmed to 25° C., and the volatiles were distilled out at reduced pressure and condensed in a cold trap at −78° C. The condensate was fractionated to give (A) 2.91 g of 2,2,2-trifluoro-1,1-bis(trifluoromethyl)ethoxysulfur trifluoride as a colorless liquid: bp 56° to 60°; $^{19}$F NMR (CCl$_3$F) δ −71.4 ppm (q, J=3.0 Hz, 9F) and 44.0 ppm (broad, 3F) and (B) 3.60 g of bis[2,2,2-trifluoro-1,1-(trifluoromethy)ethoxy]sulfur difluoride as a colorless liquid: bp 35° to 37° C. (20 mm); $^{19}$F NMR (CCl$_3$F) δ −71.7 ppm (t, J=1.5 Hz, 18F) and +32.1 ppm (broad, 2F).

EXAMPLE 6

Fluorination of Temazepam with (CF$_3$)$_2$CHOSF$_3$

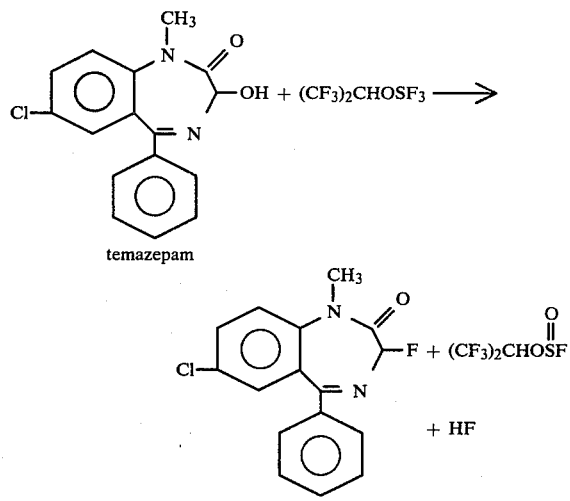

A solution of 5.12 g (0.02 mol) of 2,2,2-trifluoro-1-(trifluoromethyl)ethoxysulfur trifluoride in 25 ml of methylene chloride was cooled to −70°, and a solution of 3.0 g (0.01 mol) of temazepam in 10 ml of methylene chloride was added dropwise. The reaction mixture was warmed to room temperature, and stirred for 1 hr. Sodium fluoride, 1 g, was added, and the mixture was stirred for 10 min, filtered, and then evaporated to dryness under reduced pressure. The residue was recrystallized from ethanol to give 2.48 g (82%) of 7-chloro-3-fluoro-1,3-dihydro-1-methyl-5-phenyl-2H-1,4-benzodiazepin-2-one(3-fluorodiazepam) as a white crystalline solid: mp 142° to 144°. The latter compound is a tranquilizer as shown in U.S. Pat. No. 4,120,856.

EXAMPLE 7

Fluorination of 4-Nitrobenzyl Alcohol With (CF$_3$)$_2$CHOSF$_3$

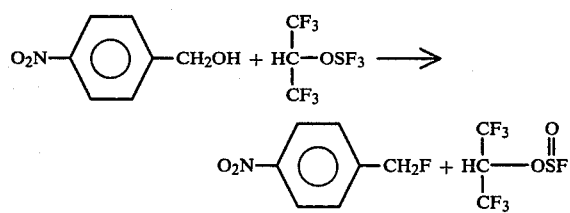

A solution of 0.77 g (5 mmol) of 4-nitrobenzyl alcohol in 15 ml of methylene chloride was added dropwise over a period of 10 min to a stirred solution of 2.0 g (7.8 mmol) of 2,2,2-trifluoro-1-(trifluoromethyl)ethoxysulfur trifluoride in 5 ml of methylene chloride cooled to 10°. The reaction mixture was warmed to room temperature and then evaporated to dryness under reduced pressure. The residue was recrystallized from pentane to give 0.59 g (76%) of 4-nitrobenzyl fluoride as colorless needles: mp 33° to 34°. Recrystallization from pentane raised the melting point to 36° to 37°.

EXAMPLE 8

Fluorination of 4-Nitrobenzyl Alcohol With [(CF$_3$)$_2$CHO]$_2$SF$_2$

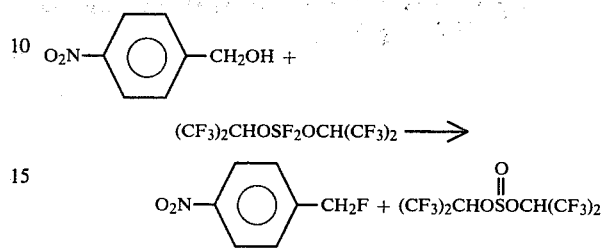

A solution of 770 mg (5 mmol) of 4-nitronbenzyl alcohol in 15 ml of methylene chloride was added dropwise to a stirred solution of 3.0 g (7.5 mmol) of bis[2,2,2-trifluoro-1-(trifluoromethyl)ethoxy]sulfur difluoride in 5 ml of methylene chloride at 25°. The reaction mixture was stirred for 18 hrs, and then evaporated to dryness under reduced pressure. The residue was recrystallized from pentane to give 490 mg (63%) of 4-nitrobenzyl fluoride as colorless needles, mp 33° to 34°. A second recrystallization raised the melting point to 36° to 37°. The 4-nitrobenzyl fluoride is a known compound useful as a chemical intermediate.

The embodiments of the invention in which an exclusive property or privilege is claimed are defined as follows:

1. Fluoroalkoxysulfur fluorides of the formula $$\left( R-\underset{\underset{CF_3}{|}}{\overset{\overset{CF_3}{|}}{C}}-O \right)_n SF_{(4-n)}$$

wherein R is selected from H, CH$_3$, CF$_3$ and C$_2$F$_5$, and n is 1 or 2.

2. Fluoroalkoxysulfur fluorides according to claim 1 wherein n=1.

3. Fluoroalkoxysulfur fluorides according to claim 2 wherein R is H.

4. Fluoroalkoxysulfur fluorides according to claim 2 wherein R is CF$_3$.

5. Fluoroalkoxysulfur fluorides according to claim 2 wherein R is CH$_3$.

6. Fluoroalkoxysulfur fluorides according to claim 2 wherein R is C$_2$F$_5$.

7. Fluoroalkoxysulfur fluorides according to claim 1 wherein n=2.

8. Fluoroalkoxysulfur fluorides according to claim 7 wherein R is H.

9. Fluoroalkoxysulfur fluorides according to claim 7 wherein R is CF$_3$.

10. Fluoroalkoxysulfur fluorides according to claim 7 wherein R is CH$_3$.

11. Fluoroalkoxysulfur fluorides according to claim 7 wherein R is C$_2$F$_5$.

12. A process for making the fluoroalkoxysulfur fluorides of claim 1, comprising reacting sulfur tetrafluoride with a lithium fluoroalkoxide of the formula

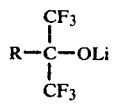
wherein R is selected from H, CH₃, CF₃, and C₂F₅.
13. A process according to claim 12 wherein the ratio of lithium fluoroalkoxide to sulfur tetrafluoride is about 3:1 to 1:10, respectively.
* * * * *
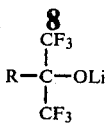
wherein R is selected from H, CH₃, CF₃, and C₂F₅.
13. A process according to claim 12 wherein the ratio of lithium fluoroalkoxide to sulfur tetrafluoride is about 3:1 to 1:10, respectively.
* * * * *